United States Patent
Hess et al.

(10) Patent No.: US 6,753,169 B2
(45) Date of Patent: *Jun. 22, 2004

(54) PRESSURE-CONTROLLED NUCLEIC ACID HYBRIDIZATION

(75) Inventors: Robert A. Hess, Brighton, MA (US); James A. Laugharn, Jr., Winchester, MA (US); David J. Green, Fitzwilliam, NH (US)

(73) Assignee: BBI, BioSeq, Inc., West Bridgewater, MA (US)

( * ) Notice: Subject to any disclaimer, the term of this patent is extended or adjusted under 35 U.S.C. 154(b) by 8 days.

This patent is subject to a terminal disclaimer.

(21) Appl. No.: 09/901,297

(22) Filed: Jul. 9, 2001

(65) Prior Publication Data

US 2001/0055772 A1 Dec. 27, 2001

Related U.S. Application Data

(63) Continuation of application No. 09/035,652, filed on Mar. 5, 1998, now Pat. No. 6,258,534.
(60) Provisional application No. 60/076,478, filed on Mar. 2, 1998.

(51) Int. Cl.[7] .............................. C12P 19/34; C12Q 1/68; C07H 21/02; C07H 21/04; C07H 19/00
(52) U.S. Cl. ........................... 435/91.2; 435/6; 435/7.1; 435/91.1; 536/22.1; 536/23.1; 536/24.3; 536/24.31; 536/24.32; 536/24.33
(58) Field of Search ............................. 530/22.1, 23.1, 530/24.3, 24.31, 24.32, 24.33; 435/6, 7.1, 91.1, 91.2

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis et al. | 435/91 |
| 5,003,047 A | 3/1991 | Yarmush et al. | 530/413 |
| 5,605,662 A | 2/1997 | Heller et al. | 422/68.1 |
| 5,632,957 A | 5/1997 | Heller et al. | 422/68.1 |
| 6,258,534 B1 * | 7/2001 | Laugharn et al. | 435/6 |
| 6,472,186 B1 * | 10/2002 | Quintanar et al. | 435/91.2 |

FOREIGN PATENT DOCUMENTS

| | | |
|---|---|---|
| WO | WO 96/27423 | 9/1996 |
| WO | WO 98/00032 | 1/1998 |
| WO | WO 99/22868 | 5/1999 |

OTHER PUBLICATIONS

Olson et al., (1989) "Recovery Of Antigens From Immunoadsorbents Using High Pressure", *BioTechnology*, (7): 369–373.

Anderson and Young (1986) "Quantitative Filter Hybridisation", *Nucleic Acid Hybridisation*, Ch 4, 73–11.

Yarmush et al.,(1992) "Immunoadsorption: Strategies for Antigen Elution and Production of Reusable Adsobents", *Biotechnol. Prog.* 8168–178.

MacGregor et al., (1996) "Sequence, Salt, Charge, and the Stability of DNA at High Pressure", *High Pressure Effects in Molecular Biophysics and Enzymology*, 149–170.

Wages, Jr. et al., (1997) "Affinity Purification of RNA: Sequence–Specific Capture by Nonionic Morpholino Probes", *Biotechniques*, 23:1116–1121.

Mozhaev et al., (1994) "Exploiting the Effects of High Hydrostatic Pressure in Biotechnological Applications", *TIBTECH*, 12:493–501.

* cited by examiner

*Primary Examiner*—Jeffrey Siew
(74) *Attorney, Agent, or Firm*—Fish & Richardson, P.C.

(57) ABSTRACT

A method of hybridizing a first nucleic acid to a second nucleic acid at least partially complementary to the first nucleic acid by (1) providing a sample vessel and pressure controller for the vessel; and (2) contacting the first and second nucleic acids within the vessel at a pressure above ambient pressure that is effective to enhance hybridization of the first and second nucleic acids.

4 Claims, No Drawings

PRESSURE-CONTROLLED NUCLEIC ACID HYBRIDIZATION

CROSS REFERENCE TO RELATED APPLICATIONS

This application is a continuation of U.S. application Ser. No. 09/035,652, filed Mar. 5, 1998, now U.S. Pat. No. 6,258,534, which claim the benefit of U.S. Provisional Application No. 60/076,478, filed Mar. 2, 1998, and of International Application No. PCT/US97/11198, filed Jul. 1, 1997.

FIELD OF THE INVENTION

The invention is in the general field of nucleic acid hybridization.

BACKGROUND OF THE INVENTION

Nucleic acid hybridization is an important technique for detecting the presence of particular sequence information. Recent advances have allowed for the production of high density oligonucleotide arrays which may have great utility for research and clinical diagnostics. Typically, a sequence is amplified and labeled with fluorescent tags. The sample is incubated with the probe array and the sample is washed with a series of increasingly stringent buffers. Stringency may be provided by means of reduced salt concentration or increased temperature. Reduced salt concentrations lead to electrostatic repulsion between phosphate groups, thereby lowering the melting temperature ($T_m$).

The number of different sequences on each array is ultimately limited by the detection capabilities of the instrument analyzing it and factors such as contaminating fluorescent compounds, stray light, and hybridization of mismatched oligonucleotides. As the stringency of hybridization is increased, the noise level from mismatches is reduced (increasing specificity), but the overall signal is also reduced due to loss of correctly hybridized molecules (decreasing sensitivity).

Two related and important amplification techniques which depend on the specificity and sensitivity of oligonucleotide hybridization are polymerase chain reaction (PCR) and ligase chain reaction (LCR), which are commonly used in medical diagnostics and research.

SUMMARY OF THE INVENTION

The invention relates to controlling the specificity, sensitivity, or selectivity of nucleic acid hybridization procedures. Control of hybridization according to the present invention is achieved through application of high hydrostatic pressure. Without intending to be limited to any mechanism, it is believed that increased pressure favors nucleic acid hybridization (i.e., reversible or irreversible hybridization). Regardless of the mechanism involved, high pressure increases the sensitivity, specificity, or selectivity of nucleic acid hybridizations.

Accordingly, the invention features a method of hybridizing a first nucleic acid to a second nucleic acid at least partially complementary to the first nucleic acid by (1) providing a sample vessel and pressure controller for the vessel; and (2) contacting the first and second nucleic acids within the vessel at a pressure above ambient pressure (e.g., above 10,000 psi) which is effective to enhance hybridization of the first and second nucleic acids. This method opitionally includes cycling pressure in the vessel between a first higher pressure at which the first and second nucleic acid are hybridized and a second lower pressure at which the first and second nucleic acid are denatured. In case of pressure cycling, can further include providing a temperature control for the sample vessel, and cycling the temperature between a lower temperature and a higher temperature, such that the first and second nucleic acids hybridize at the first pressure and lower temperature, and such that the first and second nucleic acids denature at the second pressure and higher temperature. Alternatively, the vessel can be maintained at a constant temperature as the pressure is cycled. Such methods can be used to amplify a portion of the second nucleic acid. An optional step in any of the above methods includes washing away unhybridized nucleic acids after increasing the pressure but before decreasing the pressure.

In another embodiment, the invention features a method of detecting in a sample the presence of a nucleic acid that hybridizes to a reference nucleic acid at a first higher pressure but not at a second lower pressure by (1) providing a sample vessel and pressure controller for the vessel; and in any order (2) contacting the reference sequence with the sample in the vessel at the first pressure; (3) contacting the reference sequence with the sample in the pressure vessel at the second pressure; and (4) detecting the presence of a nucleic acid that hybridizes to the reference nucleic acid at the first pressure but not at the second pressure. In one aspect, the reference sequence is first contacted with the sample and hybridization is detected, and then the pressure is lowered and the absence of hybridization is detected.

The invention also features a method of discriminating between a first nucleic acid and a second nucleic acid that is different from the first nucleic acid by (1) providing a sample vessel and pressure controller for the vessel; (2) maintaining the vessel at a constant pressure; (3) providing the first and second nucleic acid and a reference nucleic acid in the vessel under conditions that do not allow either the first or the second nucleic acid to hybridize to the reference nucleic acid; (4) perturbing at least one condition (e.g., temperature or an electric field) to establish conditions that permit the first nucleic acid to form a complex with the reference nucleic acid at equilibrium and to permit the second nucleic acid to form a complex with the reference nucleic acid at equilibrium; and (5) comparing the time necessary to achieve equilibrium hybridization between the first nucleic acid and the reference nucleic acid with the time necessary to achieve equilibrium hybridization between the second nucleic acid and the reference nucleic acid, wherein the difference indicates the relative difference in sequence between the first and the second nucleic acids.

In addition, the invention features a method of discriminating between a first nucleic acid and a second nucleic acid that is different from the first nucleic acid by (1) providing a sample vessel and pressure controller for the vessel; (3) providing the first and second nucleic acid and a reference nucleic acid in the vessel under a first pressure that does not allow either the first or the second nucleic acid to hybridize to the reference nucleic acid; (4) perturbing the pressure to establish conditions that permit the first nucleic acid to form a complex with the reference nucleic acid at equilibrium and to permit the second nucleic acid to form a complex with the reference nucleic acid at equilibrium; and (5) comparing the time necessary to achieve equilibrium hybridization between the first nucleic acid and the reference nucleic acid with the time necessary to achieve equilibrium hybridization between the second nucleic acid and the reference nucleic acid, wherein the difference indicates the relative difference in sequence between the first and the second nucleic acids.

Methods of placing nucleic acids and optionally enzymes under pressure are described in WO 96/27432.

To facilitate understanding of the invention, a number of terms are defined below.

As used herein, the term "solution" refers to a liquid, and more particularly, the incorporation of substances (e.g. dissolved compounds) in a liquid. The term "aqueous solution" refers to a solution either containing water or that is like water. For example, the present invention contemplates the use of assay buffers that are aqueous solutions.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the terms "nucleic acid" and "nucleic acid substrate" encompass both DNA and RNA, whether single or double stranded. It is not intended that the present invention be limited by the length of the nucleic acid; the nucleic acid may be genomic or a defined length (e.g. short oligonucleotides) or fragments thereof (including single bases). It is also not intended that the present invention be limited by the nature or source of the nucleic acid. It may be naturally occurring, purified, produced synthetically, recombinantly or by amplification. The term "modified nucleic acid substrate" refers to the alteration of the structure of the nucleic acid substrate. To illustrate, an enzyme may remove a nucleotide from the nucleic acid substrate, yielding a modified nucleic acid substrate.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "sample" is used in its broadest sense. That is, the term may encompass a specimen, culture, biological sample, environmental sample, etc. The term includes human and animal samples as well as naturally occurring and synthetic material. The term "sample vessel" is used to indicate a means for containing a sample, whether by enclosing a sample (e.g., in a batch format) or by using a sample in an enclosed device (e.g., channeling both within and between a chamber, channel or stream). Similarly, a "reaction vessel" is not limited to any one design; typically it is a sample vessel in which a reaction takes place.

A "reaction mixture" refers to the mixing together of two or more components such that a reaction will occur. The term "optimum enzymatic temperatures" refers to those temperatures at which an enzyme is most active. Thus, it depends on the characteristics of the individual enzyme. Typically, the optimum is between approximately 10 and approximately 80 degrees Centigrade, and more particularly between approximately 25 and 37 degrees Centigrade.

As used herein, the term "inhibition" of enzyme activity be pressure refers to an enzyme that is reversibly inhibited at a particular pressure. When the pressure is altered (for example, lowered), the enzyme resumes its level of original activity.

As used herein the terms "substantially inactive" and "rendering substantially inactive" refer to an enzyme that exhibits less than approximately 20%, and generally less than 10%, of its activity at optimum enzymatic temperature (100% activity). An enzyme that has been rendered substantially inactive may also exhibit no activity, but may be reversibly inhibited such that activity of approximately normal levels returns under appropriate conditions of pressure, temperature and the like.

As used herein, the term "primer" refers to an oligonucleotide, whether occurring naturally as in a purified restriction digest or produced synthetically, which is capable of acting as a point of initiation of synthesis when placed under conditions in which synthesis of a primer extension produce which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, which is capable of hybridizing to another oligonucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

As used herein, the term "target" refers to the region of nucleic acid bounded by the primers used for detection and/or amplification (e.g., by the polymerase chain reaction). Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleoside triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

Enzymes that synthesize polymers may dissociate after each catalytic event, i.e., they may be "nonprocessive." On the other hand, they may remain bound to the polymer until many cycles of reaction are completed, i.e., they may be "processive." See A. Kornberg, *DNA Replication* (Freeman and Co. 1980).

Other features or advantages of the present invention will be apparent from the following detailed description and from the claims.

DETAILED DESCRIPTION OF THE INVENTION

The invention is based on the realization that the molar volumes of mismatched nucleic acid hybridization products are larger than the molar volumes for complementary hybridization products. Thus, high pressure will tend to drive the hybridization reaction equilibrium towards correct matches and away from mismatches and result in a higher signal to noise ratio in a given hybridization. Higher temperatures may also-be employed for a further decrease in mismatching. Dissociation of fully complementary nucleic acids can be slowed by high pressure, whereas dissociation of mismatched sequences can be enhanced or slowed to a lesser degree than fully complementary hybrids. Pressure effects on melting and dissociation may provide information that allows assignment of a mismatched base with fewer than four probes or may increases the sensitivity of a hybridization reaction.

Modulation of hydrostatic pressure has multiple advantages in hybridization assays. Pressure allows rapid modulation of the stringency of hybridization. By raising the melting temperature of hybrids, higher hybridization temperatures may be used with the advantage of more rapid approach to equilibrium. Pressure differs from other forms of stringency modulation such as salt concentration or temperature in that it provides additional discrimination between match and mismatch. This is of particular advantage when the base to be discriminated is at or near the terminus of one of the sequences to be assayed. The additional sensitivity provided by increased specificity under pressure allows for multiple benefits, such as more rapid data collection, higher density arrays, and shorter hybridization times. Pressure operates without exchange of fluids and may be transmitted at up to the speed of sound.

Several devices may be used for the application of hydrostatic pressure to hybridization reactions, arrays or microchip-based hybridization arrays. The reaction may be sealed in a deformable container and the container is placed in a device that generates elevated hydrostatic pressures and is temperature controlled. After the hyperbaric hybridization reaction is complete, the reaction is removed from the pressurizing apparatus and analyzed by the various means known in the art.

Another useful device is a hyperbaric chamber with an optical window. Such devices are known in the art of high pressure science and include the diamond anvil cell, the sapphire anvil cell and fiber-optic feed-throughs into hyperbaric chambers (Eremets, M "High Pressure Experimental Methods", 1996, Oxford University Press: New York). With this device, the effects of changing the pressure or temperature may be measured continuously. For example, the rate of strand dissociation in a hybridization array may be measured after a rapid pressure drop to yield sequence information. This experiment may make use of the knowledge that pressure reduces the rate of hybrid melting so that by raising the pressure and then the temperature, one can put the system in a state of non-equilibrium which is high in potential energy. The pressure is then released and the rate of strand melting is measured.

Alternatively, a hybridization reaction may be conducted at low effective stringency by being conducted at high pressure. The pattern of hybridization to a defined polynucleotide array is determined by optical or other means. The pressure is then reduced to lower the stringency, and the change in the pattern of bound DNA is again determined, optionally after flushing away nucleotides which were released. Further cycles of pressure lowering and optional flushing allow determination of the degree of affinity of the bound DNA to the array.

In a method of the invention, the hybridization reaction is allowed to come to equilibrium while under stringent conditions at an elevated hydrostatic pressure, such as 100,000 psi. The reaction is then washed with a mildly stringent buffer and the hybridization pattern is determined.

In another method of the invention, the hybridization reaction occurs under conditions of low stringency and then is washed under conditions of high stringency while under pressure. A device suitable for this purpose is ("Version3") described in WO 96/27432. Other devices such as those utilizing electrophoresis or electroosmosis may be used. The washing solution may be held under pressure and then rapidly replaced with a non-stringent solution at atmospheric pressure, provided the exchange is rapid enough that the system does not significantly return to a condition of reduced selectivity.

The extent of sequence-specific hybridization is determined by measurement of the rate of relaxation toward equilibrium following a perturbation such as a rapid temperature jump at several hydrostatic pressures. The pressure effect on the rate of approach to equilibrium will be a sensitive discriminator of matched vs. mismatched sequences and will allow for a well-defined and more easily measured dissociation rate. In addition, singly and multiply mismatched sequences will be more easily determined. The measured dissociation rate at high pressure may be sufficient to accurately discriminate between mismatches.

Another perturbation which may be used in this technique is electrical perturbation as described in U.S. Pat. Nos. 5,632,957 and 5,605,662 and involves monitoring changes in fluorescence while short pulses of electric field perturbations are applied.

Since the methods of the invention results in increased specificity, sensitivity, or selectivity of hybridization, such methods can be used to reduce mis-primings in technological applications involving polymerase or ligase enzymes, which require hybridization of a primer to a template. Examples include PCR, Sanger sequencing reactions, and LCR. Hybridizations may be done under high pressures such as 10,000 psi or 100,000 psi. It is possible to find a pressure at which the optimal hybridization temperature is the same as the optimal temperature for polymerase extension, thereby decreasing the number of thermal cycling steps needed for any suitable application. In addition, it is anticipated that fewer errors will result in polymerase extension reactions at elevated pressures the specificity of the editing mechanism is increased due to increased exonuclease activity. Optimal pressures for hybridization and extension steps may differ and are expected to be in the range of 5000 psi to 100,000 psi. High pressures have the added advantage of further stabilizing the thermostable enzymes which are often used in these reactions.

Improved Biochip Array Performance

An important application for the techniques and apparatus of the invention is in the improved speed and accuracy of readout in "sequencing by hybridization" and in the closely related, currently-commercial techniques applied to gene identification and diagnosis. In these techniques, an array of single-stranded nucleic acids—usually DNA, or less commonly RNA, and in principle including non-natural nucleic acids such as "peptide" nucleic acids—is synthesized on the surface of a "chip", of silicon, silica/glass, or other planar material. Techniques derived from microelectronics—in particular, sequential use of masks followed by chemical development, sometimes optically stimulated—allow the simultaneous synthesis of differing sequences of nucleic acids in different areas of the same chip. (The principles are extensively described in the literature, and are known in the art.) The resultant pattern can be used for gene diagnosis, or for sequencing of DNA.

To use the nucleic acid chips, the nucleic acids to be tested are labeled in any known manner, typically with one or more fluorescent labels. The nucleic acids are then rendered single-stranded, if necessary, and allowed to hybridize with the single stranded nucleic acids on the chip. The pattern of hybridization allows at least partial determination of the sequence of the tested nucleic acid, since the sequence of the areas of the chip to which the tested nucleic acids hybridized are known.

However, mismatches during hybridization are possible. For example, a chip sequence of 8 nucleotides will bind tested sequences in which 8, 7, 6, or even 5 or less of the bases within the nucleic acid are properly base-paired, depending on the "stringency" of the hybridization conditions. The concept of "stringency" is well-known in the art. In essence, when the conditions in the test solution (e.g., salt concentration, buffer composition, pH and temperature) favor binding, the hybridization conditions are described as "less stringent" or "of low stringency". When conditions are less favorable to hybridization, then only well-matched sequences will hybridize, and the conditions are described as "stringent", or "more stringent". Under ideal stringency, only the target sequence of interest (e.g., a perfectly complimentary sequence) will hybridize to a reference nucleic acid.

In diagnosis of genetic shifts, if a sample of DNA is restricted, labeled, and rendered single-stranded, then with an ordered array of nucleic acids on the test chip, and at high stringency, only sequences specific to the various alleles of the gene in question will bind. However, in actual situations, and in particular when amplification means are not used, many different restriction fragments of the genome will have some affinity for the array, and at low stringency, binding of test nucleic acid to most portions of the array will occur. On the other hand, at high stringency, hybridization will be slow even for well-matched nucleic acids, and may tend to be incomplete, resulting in loss of signal.

Therefore, as a practical matter, such tests are usually initiated at low stringency, where reactions are fast and quantitative, and then the stringency is gradually increased by increased temperature and/or lower ionic strength, and at the end of the process only highly homologous nucleic acids are still hybridized to the chip. The last nucleic acids to dissociate are normally the best matched to that particular area of the chip, and therefore are judged to be substantially similar to the target sequence.

While these procedures can be effective, they are also slow. With typicaly hybridization times of many minutes for each step of increased stringency, arriving at optimal conditions can take up to a few hours. The essence of the invention is the application of control of hybridization stringency by pressure. As noted above, pressure changes are very rapid, and have a characteristic time of equilibration of less than a microsecond in small volumes. One can thus arrange a continuous or pulsed flow of buffer of constant composition, and conduct the stringency analysis by decreasing the pressure. The speed of successive steps of increased stringency is limited only by the time required for less stringently bound nucleic acids to dissociate from the reference nucleic acid. Moreover, the speed of hybridization is increased at higher pressure, so the initial low-stringency hybridization step is also faster. As noted above, the time required for dehybridization, as well as any optical or other signals generated by dehybridization, may also be a factor in sequence determination.

Because the capital cost of the sequencing-by-hybridization equipment is a significant portion of the cost of performing such an assay, the use of pressure changes to control hybridization (in place of the usual temperature and/or buffer change) can increase the speed and accuracy of the analysis, which in turn can significantly lower the cost of such assays.

A system to perform such pressure-hybridization assays is also a part of the invention. The mechanical portions of such a device have previously been described in WO 96/27432. The device includes a pressurizable chamber with means for rapid pressure changes between atmospheric and a higher pressure (such as 5,000, 10,000, or 50,000 psi), and means for introduction and removal of fluids. The device is adapted to improve sequencing-by-hybridization by inclusion of a chip or slide bearing defined immobilized nucleic acid sequences in known areas, and a flow arrangement which efficiently washes the nucleic acid-bearing surface(s) of the chip with a buffer, to remove unhybridized nucleic acids, and a means for detecting the extent of dehybridization and the pattern of remaining hybridization on the chip.

The detection means may be any means known in the art which are compatible with the high pressures and sudden pressure changes necessary for the assays. The currently-preferred means for detection of hybridized test DNA is a fluorescent label, and the detection is accomplished by direct visualization. To use this system, the pressurizable chamber is provided with an optical window which allows accurate projection of emitted fluorescent light onto a detection means, such as a video camera or a photodiode array. A suitable means is an imaging lens embedded in the wall or end of the pressurizable reaction volume, which images the surface of the chip to an outside detection means. An intermediate adaptable lens, with position and/or optical power controlled electronically, and preferably located outside the pressurizable zone, can be used to correct distortions arising from changes in pressure on the imaging lens. Another option is a flat sapphire window, with an adjustably-positioned detection device, as is known from the literature related to the analytical ultracentrifuge.

Alternatively, the detection means could be a light-sensitive diode array mounted behind the nucleic acid array-bearing chip, baffled so that fluorescent light emitted from a defined area of the array falls on a particular diode or diodes, with a suitable pressure-resistant cable for conduction signals to an outside display and recording means, such as a computer.

As noted above, the effects of pressure will be beneficial in performing various sorts of nucleic acid amplification assays. These are described here in terms of some well-known DNA amplification methods, and are also applicable to amplification of other types of nucleic acids.

Nucleic Acid Amplification under High Pressure

Polymerase Chain Reaction (PCR).

In this widely practiced method, a particular sequence of DNA, typically a restriction fragment, is amplified by use of a primer, or preferably two primers, and a DNA polymerase, in the presence of four deoxyribonucleoside triphosphates (dNTPs). The primer is allowed to hybridize, at a first hybridization-permissive temperature, to a stretch of ssDNA to be amplified. Then the polymerase, which requires a short sequence of double-stranded DNA as a "start" point, will proceed along the DNA to make a copy of it. If there are two primers, then amplification proceeds on both strands. Next, the reaction mixture is heated to dissociate the newly-formed copies from the original. On cooling, new primers hybridize, and the cycle is repeated. In principle, the numbers of copies of the target DNA is doubled in each cycle, leading to a large increase in the amount of the target DNA sequence.

The amplified copies can be fluorescently labelled. If di-deoxy nucleotides are used in the last few cycles, then the resultant mixture can be used for Sanger-type sequencing.

High pressure offers three distinct avenues for improvement of the PCR.

First, it can be used to replace the temperature-cycling step with a pressure controlled dehybridization/hybridization cycle. This is inherently faster and allows a "quick-start" procedure. In the high-pressure-PCR (HP-PCR) assay, the polymerase's sensitivity to pressure is determined, and a first pressure P3 is selected. P3 is low enough to retain enzymic activity and high enough to enable primer binding. A temperature T1 is selected at which the enzyme can function, and at which the primers (and primer extension products) will be dehybridized from the test DNA at low pressure. Typically, enzymes that are thermostable have enhanced tolerance to hyperbaric conditions. This temperature (T1) can be predicted from first principles and the primer sequence composition, and quickly optimized to the actual situation.

The reaction mixture is prepared at an initial P1/T1 state, except for the polymerase, and is raised to the P3/T1 state. The primers hybridize to the template. Enzyme is added under pressure and the primers are extended at a P2/T1, where P2 can be between P1 and P3. After the new strands have been polymerized, the pressure is dropped to P1 at which the primers and extension products will dehybridize. The pressure is raised back to P3/T1 and held briefly to allow primer hybridization/extension before progressing to P2/T1 for primer extension. Then pressure is reduced to P1/T1, and the cycle is repeated. The consequences at the P1/T1, P2/T1, and P3/T1 states are summarized below.

|  | P1/T1 | P2/T1 | P3/T1 |
| --- | --- | --- | --- |
| Enzyme active | Yes | Yes | Yes |
| Primer & template bind | Yes | No | Yes |
| Primer & template denature | Yes | No | No |
| Primer extends | No | Yes | N/A |
| Double-strand denatures | Yes | No | No |

The reactions immediately above were conducted at one temperature, T1, to illustrate one example of the methods of this invention. However, performing reactions at different temperatures in conjunction with different pressures can be ideal under some circumstances.

Because pressure changes propagate through the medium at the speed of sound, and require no convection or mixing, pressure changes can occur throughout a medium much quicker than temperature changes. Consequently, the reaction medium spends more time at equilibrium. Therefore, the time required to conduct a PCR reaction is reduced. Since PCR is important in genome sequencing, and increasing in forensics and diagnostics, the decrease in time required is advantageous.

Second, careful selection of temperatures and pressures can increase the performance of an enzyme. As noted above, in many cases it will be possible to find a temperature and pressure combination at which the activity of the enzyme is optimized, which will shorten the time required in the polymerization step. This speed improvement is independent of the speed improvement obtained by pressure changes. In addition, by selection of temperature and pressure, the stability of the enzyme against denaturation or other inactivation can be enhanced. In particular, the same optimum pressure for activity will normally suffice to prevent enzyme denaturation, because the additional cycling step involves a decrease in pressure (disfavoring enzyme denaturation) rather than an increase in temperature (favoring enzyme denaturation). This may allow additional kinds of polymerases to be used in PCR.

Moreover, at some combinations of temperature and pressure, the polymerase will be more tightly bound to the DNA being replicated, and is expected to exhibit increased processivity, resulting in longer strands on average, and a higher proportion of fully replicated strands in the mixture. This is critical when using PCR to amplify long stretches of DNA, for example 1000 bases or more.

Third, running the PCR at high pressure is especially beneficial because the effective stringency of the reaction can be improved at high pressure. Improvement of stringency is described above in the discussion of "DNA chips". Because pressure widens the temperature spread between hybridization of matched and mismatched primers, binding of primers to mismatched sites can be significantly reduced at high pressure compared to ambient pressure. The speed of change between dehybridizing and hybridizing conditions can also diminish the proportion of mismatched hybridizations in the mixture. In turn, there will be fewer errors in the amplified sequences, resulting in better quality (via higher fidelity of polymerization) of the amplified DNA for its intended use, such as for sequencing, or as a probe for use in a reaction involving a DNA chip.

In addition, the primers can be shorter in a high-pressure reaction, because formation of double-stranded regions is favored at high pressure. Current practice favors longer primers both for specificity and sensitivity of hybridization. With pressure, and particularly when specificity within the genome is less critical, primers as short as eight to ten nucleotides can be used.

Ligase Chain Reaction (LCR).

In LCR, the two primers are directed to the same strand, and are contiguous. If a target strand is present in the DNA to be tested, both primers hybridize to adjacent sequences on the target. A DNA ligase is added to join the strands. The ligated product is dissociated by an increase in temperature, and the process repeats after cooling. The presence of ligated DNA is detected by any of several means (e.g., molecular weight or fluorescence energy transfer).

Essentially all of the advantages of pressure cycling in the PCR apply to the LCR. The increased selectivity for accurately matched probes is particularly critical in LCR, since it is less sensitive than the PCR to single-base substitutions and deletions, especially away from the ligation site.

Other Amplification Methods.

There are now over a dozen other methods of nucleic acid amplification. Most of these require a hybridization/dehybridization cycle. The use of pressure cycling as a replacement for temperature cycling will be feasible in any such amplification reaction.

Without further elaboration, it is believed that one skilled in the art can, based on the above disclosure and the examples below, utilize the present invention at its fullest extent. The following examples are to be construed as merely illustrative of how one skilled in the art can practice the invention and are not limitative of the remainder of the disclosure in any way. Any publications cited in this disclosure are hereby incorporated by reference.

EXAMPLE 1

Hybridization Under High Pressure

The purpose of this example is to show an increased discrimination between matched and mismatched hybridizations when the hybridization is performed at a pressure above ambient pressure.

A known sequence of single-stranded DNA is immobilized on glass using standard techniques. For example, the DNA is synthesized so as to have a terminal amine, which is reacted with groups covalently bound to the glass. Two probes are made, each twelve base-pairs long and complementary to a region of the immobilized DNA. A mismatch error is introduced during synthesis into one of the two probes. Each probe is also fluorescently labeled during synthesis.

Buffer (pH, salt) and temperature conditions are determined at which the matched probe is bound to the slide and the mismatched probe is not. (These can be estimated by known methods, since the sequences are known, and can be determined empirically.) The temperature is selected to be the lowest temperature at which the matched probe is bound and the mismatched probe is not. Then the temperature increase needed to dissociate the bound matched probe is determined.

The experiment is repeated, using the same probes and slides, at high pressure, for example 10,000 psi. Both probes can be found to be bound.

The buffer is then changed by reduction of its ionic strength until the mismatched probe is not bound and the matched probe is bound at ambient pressure. Then the temperature is increased in increments, until the matched probe is no longer bound, and the required temperature increase is determined. This increase can be found to be greater than the temperature increase required at ambient pressure.

EXAMPLE 2

Stringent Washing of Hybrids Under High Pressure

The purpose of this example is to show an increased discrimination between matched and mismatched hybridizations when the hybridization reaction is washed under high pressure.

Slides are established in a flow cell for efficient washing with measurable amounts of buffer. Using the conditions as established in Example 1, the probes are bound to the slide at high pressure at a temperature and buffer concentration sufficient to allow the mismatched probe to be bound. Then the pressure is reduced to one known to allow dissociation of the mismatched probe, and the amount of buffer required to elute the mismatched probe is determined. The experiment is repeated at atmospheric pressure, but the buffer concentration is changed to allow dissociation of the mismatched probe. The required volume is determined. The dissociation volume can be greater at lower pressure.

EXAMPLE 3

Measurement of Melting Temperature Differences for Matched vs. Mismatched Oligonucleotide Hybrids as a Function of Pressure An immobilized DNA array containing DNA of various sequences is constructed by standard methods described in the literature. A mixture of probes with various degrees of matching to portions of the array is subjected to the manipulations described in Examples 1 and 2 above. It is observed that the discrimination among probes is significantly improved when the entire procedure is conducted at a constant high pressure and is further improved by variation of the stringency by alteration of the pressure (e.g., at high pressure) compared to alteration of the buffer composition or the temperature.

EXAMPLE 4

Measurement of Pressure Effect on Temperature-Jump Relaxation Rate

Double stranded DNA of known sequence is denatured at atmospheric pressure and at elevated temperature by a temperature jump. Denaturation is observed by a downward shift in UV absorption of the nucleic acids. It is found that the rate of absorbance change is faster when the denaturation occurs at higher pressure. dsDNA with a single mismatch is found to dissociate with a similar rate, with a wider difference in the critical temperature compared to matched DNA.

EXAMPLE 5

Electric Field Modulation of Hybridization Under High Pressure

Changes in electric field can also be used to affect hybridization conditions in conjunction with high pressure. Suitable procedures and devices are described in U.S. Pat. Nos. 5,632,957 and 5,605,662. Such procedures and devices include a system for performing molecular biological diagnosis, analysis and multi-step and multiplex reactions utilizing a self-addressable, self-assembling microelectronic system for actively carrying out controlled reactions in microscopic formats. These reactions include most molecular biological procedures, such as nucleic acid hybridization, antibody/antigen reaction, and clinical diagnostics. Multi-step combinatorial biopolymer synthesis may be performed. A controller interfaces with a user via input/output devices, preferably including a graphical display. Independent electronic control is achieved for the individual microlocations. The controller interfaces with a power supply and interface, the interface providing selective connection to the microlocations, polarity reversal, and optionally selective potential or current levels to individual electrodes. A system for performing sample preparation, hybridization and detection and data analysis integrates multiple steps within a combined system. Charged materials are transported preferably via free field electrophoresis. DNA complexity reduction is achieved preferably by binding of DNA to a support, followed by cleaving unbound materials, such as by restriction enzymes, followed by transport of the cleaved DNA fragments. Active, programmable matrix devices are formed in a variety of formats, including a square matrix pattern with fanned out electrical connections, an array having electrical connections and optionally optical connections from beneath the specific microlocations.

EXAMPLE 6

Hyperbaric Amplification of DNA

Preparation of reagents: Reagents and control template DNA (531-bp human GADPH insert contained within pAMP1 UDG cloning vector) from a DNA amplification kit (Cat. # 10200-012, Life Technologies, Gaithersburg, Md.) is added to a sterile 0.5 ml amplification tube placed on ice to achieve a volume of 99 $\mu$l. One $\mu$l of Taq DNA polymerase (5 units) is added to the tube. The contents of the tube are mixed, then centrifuged briefly. A 50 $\mu$l aliquot of the reaction mixture is removed from the amplification tube and inserted into a sterile polypropylene capsule placed on ice. The 50 $\mu$l sample remaining in the amplification tube (Sample A), and the 50 $\mu$l sample in the polypropylene capsule (Sample B) are both overlaid with two drops of silicone oil.

DNA amplification using a thermocycling procedure: Sample A is placed in a thermocycler (Techne, Princeton, N.J.) set at 80° C. After 5 minutes at 80° C., Sample A is subjected to 30 cycles of amplification. Each amplification cycle is comprised of a DNA denaturing step at 94° C. for 30 seconds, a DNA annealing step at 60° C. for 75 seconds, and a DNA extension step at 72° C. for 2 minutes. At the end of the 30 cycles, the temperature is maintained at 72° C. for 10 minutes. The total elapsed time for the entire DNA amplification procedure is approximately 4 hours. The temperature is then maintained at 4° C. until an aliquot of the sample is removed for analysis by agarose gel electrophoresis, as described below.

DNA Amplification using a hyperbaric cycling procedure: Sample B was placed in a the reaction chamber of a hyperbaric cycling reactor (BioSeq, Woburn, Mass.) set at 94° C. After 5 minutes at 94° C., Sample B was subjected to 30 cycles of amplification. Each amplification cycle is comprised of a DNA denaturing step at 94° C. for 30 seconds at atmospheric pressure, a DNA annealing step at 94° C. for 1 minute at 80,000 psi, and a DNA extension step at 94° C. for 2 minutes at 80,000 psi. At the end of the 30 cycles, the temperature is lowered to 72° C. for 10 minutes. The total elapsed time for the entire DNA amplification procedure is approximately 2 hours. The temperature is then maintained at 4° C. until an aliquot of the sample is removed, at the same time as Sample A, for analysis by agarose gel electrophoresis, as described below.

Agarose gel analysis of the amplification products: One $\mu$l aliquots of Sample A and Sample B are mixed with 9 $\mu$l of an agarose gel containing ethidium bromide loading buffer. The samples are then applied to a 1.0% agarose mini-gel, and electrophoresed at 100 V for 40 minutes. DNA in the samples is quantified by UV illumination and photography. Both samples contained approximately 100 ng of DNA per 1 $\mu$l of sample.

What is claimed is:

1. A nucleic acid amplification method, comprising:
   (1) providing a sample vessel and temperature and pressure controllers for the vessel;
   (2) providing a first nucleic acid to he amplified, a nucleic acid primer that is at least partially complementary to the first nucleic acid, a DNA polymerase, and four deoxyribonucleoside triphosphates; wherein the primer has a nucleotide sequence that hybridizes to an internal nucleotide sequence in the first nucleic acid, the primer capable of being extended at least one nucleotide by the polymerase using the first nucleic acid as a template;
   (3) increasing the temperature in the vessel to a temperature effective to cause denaturation of the first nucleic acid;
   (4) increasing pressure in the vessel to a pressure above ambient pressure that allows hybridization between the denatured first nucleic acid and the primer; and
   (5) allowing the DNA polymerase to extend the primer rising the denatured first nucleic acid as a template, thereby making a copy of a least part of the first nucleic acid.

2. The method of claim 1, further comprising:
   (6) decreasing pressure to a pressure at which the first nucleic acid again dissociates; and
   (7) repeating steps (4)–(6) to further amplify the first nucleic acid.

3. The method of claim 1, wherein the primer is labelled.

4. A method of hybridizing a First nucleic acid to a second nucleic acid at least partially complementary to the first nucleic acid, the method comprising:
   (1) providing a sample vessel and pressure controller for the vessel;
   (2) contacting the first and second nucleic acids within the vessel at a pressure above ambient pressure that is effective to enhance hybridization of the first and second nucleic acids,
   (3) further providing a nucleic acid polymerase and at least one nucleotide triphosphate and wherein the first nucleic acid has a 3' terminal nucleotide that hybridizes to an internal nucleotide in the second nucleic acid, the first nucleic acid capable of being extended at least one nucleotide by the polymerase using the second nucleic acid as a template; and
   (4) cycling pressure in the vessel between a first higher pressure at which the first and second nucleic acid are hybridized and a second lower pressure at which the first and second nucleic acid are denatured, wherein a portion of the second nucleic acid is amplified.

* * * * *

UNITED STATES PATENT AND TRADEMARK OFFICE
CERTIFICATE OF CORRECTION

PATENT NO. : 6,753,169 B2
DATED : June 22, 2004
INVENTOR(S) : Robert A. Hess, David J. Green and James A. Laugharn, Jr.

It is certified that error appears in the above-identified patent and that said Letters Patent is hereby corrected as shown below:

Column 1,
Line 8, delete "claim", insert -- claims --.

Column 16,
Line 9, delete "rising", insert -- using --.
Line 18, delete "First", insert -- first --.

Signed and Sealed this

Eighth Day of November, 2005

JON W. DUDAS
*Director of the United States Patent and Trademark Office*